US010821216B1

(12) United States Patent
Collins et al.

(10) Patent No.: US 10,821,216 B1
(45) Date of Patent: Nov. 3, 2020

(54) METHOD AND APPARATUS FOR A HEMODIAFILTRATION MODULE FOR USE WITH A DIALYSIS MACHINE

(71) Applicant: Nephros Inc., South Orange, NJ (US)

(72) Inventors: Gregory Collins, Monroe, NY (US); Daron Evans, Woodside, CA (US); Andy Uchida, Los Altos, CA (US)

(73) Assignee: NEPHROS INC., South Orange, NJ (US)

( * ) Notice: Subject to any disclaimer, the term of this patent is extended or adjusted under 35 U.S.C. 154(b) by 188 days.

(21) Appl. No.: 16/026,825

(22) Filed: Jul. 3, 2018

Related U.S. Application Data

(60) Provisional application No. 62/528,292, filed on Jul. 3, 2017.

(51) Int. Cl.
| | |
|---|---|
| *B01D 61/28* | (2006.01) |
| *B01D 61/24* | (2006.01) |
| *B01D 61/32* | (2006.01) |
| *A61M 1/34* | (2006.01) |
| *A61M 1/16* | (2006.01) |
| *A61M 1/36* | (2006.01) |
| *A61M 39/24* | (2006.01) |
| *A61M 1/10* | (2006.01) |

(52) U.S. Cl.
CPC ........ *A61M 1/3417* (2014.02); *A61M 1/1039* (2014.02); *A61M 1/1605* (2014.02); *A61M 1/3437* (2014.02); *A61M 1/3465* (2014.02); *A61M 1/3663* (2013.01); *A61M 39/24* (2013.01); *A61M 2205/126* (2013.01)

(58) Field of Classification Search
CPC .............. A61M 1/3417; A61M 1/1039; A61M 1/1605; A61M 1/3437; A61M 1/3663; A61M 39/24; A61M 2205/126
See application file for complete search history.

(56) References Cited

U.S. PATENT DOCUMENTS

| | | |
|---|---|---|
| 6,303,036 B1 | 10/2001 | Collins et al. |
| 6,315,895 B1 | 11/2001 | Summerton et al. |
| 6,719,907 B2 | 4/2004 | Collins et al. |
| 6,916,424 B2 | 7/2005 | Collins et al. |
| 7,285,106 B2 | 10/2007 | Collins et al. |
| 7,306,736 B2 | 12/2007 | Collins et al. |
| 7,775,375 B2 | 8/2010 | Palumbo et al. |

*Primary Examiner* — Dirk R Bass
(74) *Attorney, Agent, or Firm* — Leason Ellis LLP

(57) ABSTRACT

A method and apparatus are provided for a hemodiafiltration delivery module that is used in conjunction with a UF controlled dialysis machine to enable hemodiafiltration therapy to be performed. The advantage is that one can fully utilize a current functioning dialysis machine to perform a hemodiafiltration therapy as opposed to purchasing a completely new machine that offers this capability.

9 Claims, 5 Drawing Sheets

METHOD AND APPARATUS FOR A HEMODIAFILTRATION MODULE FOR USE WITH A DIALYSIS MACHINE

CROSS-REFERENCE TO RELATED APPLICATION

The present application claims priority to and the benefit of U.S. provisional application Ser. No. 62/528,292, filed Jul. 3, 2017, which is hereby incorporated by reference in its entirety.

TECHNICAL FIELD

The invention relates to blood cleansing systems in general and, more particularly, to a blood cleansing modality commonly referred to as hemodiafiltration.

BACKGROUND

Hemodiafiltration combines both standard hemodialysis and hemofiltration into one process, whereby a dialyzer cartridge containing a high flux membrane is used to remove substances from the blood both by diffusion and by convection. The removal of substances by diffusion is accomplished by establishing a concentration gradient across a semipermeable membrane by flowing a dialysate solution on one side of the membrane while simultaneously flowing blood on the opposite side of the membrane. In existing systems, to enhance removal of substances using hemodiafiltration, a solution called substitution fluid is continuously added to the blood either prior to the dialyzer cartridge (pre-dilution) or after the dialyzer cartridge (post-dilution). In a dual-stage cartridge design (U.S. Pat. No. 6,719,907 which is incorporated by reference in its entirety), substitution fluid can also be introduced directly into a port on the dialyzer filter cartridge in a mid-dilution mode. An amount of fluid equal to that of the added substitution fluid is ultrafiltered across the dialyzer cartridge membrane carrying with it additional solutes.

Substitution fluid can be purchased as a sterile/non-pyrogenic fluid (e.g., 0.9% saline solution or Ringer's Lactate solution) contained in large flexible bags. The disadvantage of using this type of fluid for hemodiafiltration is the relatively high cost associated with using large volumes during treatment. As a result, methods have been developed for producing substitution fluid on-line by filtration of a non-sterile dialysate through a suitable filter cartridge rendering it sterile and non-pyrogenic. Techniques for online production of substitution fluid have been described in the literature and are well known by one skilled in the art. Here, a series of filter cartridges and a substitution pump were used in conjunction with a dialysis machine as a means to generate on-line substitution fluid for the purposes of performing hemodiafiltration. What is not described, however, is how the substitution pump is operated when the blood pump stops or when the dialysis machine goes into bypass which prevents dialysate being delivered to the dialyzer and substitution pump. It is understood by those skilled in the art, that a dialysis machine may suddenly stop the blood pump or go into a dialysate bypass mode in response to a machine alarm condition (e.g., due to excessive extracorporeal circuit pressure or a low or high dialysate conductivity reading). When this happens, the substitution pump should be disabled or turned OFF as a means to prevent a potentially hazardous condition from occurring (e.g., an occurrence of hemoconcentration as a result of continued delivery of substitution fluid when blood flow substantially decreases or ceases).

Dialysis machine manufacturers have developed stand-alone dialysis machines with on-line substitution fluid suitable for hemodiafiltration. One example is the Fresenius OnLine Plus™ System, available from Fresenius Medical Care of Bad Homburg, Germany. A second example, available from Gambro AB of Lund Sweden, has been described in the literature. In these systems, control of the substitution fluid pump by the dialysis machine is coordinated in such a manner as to prevent unsafe or hazardous conditions.

In general, dialysis machines are replaced every seven years on average and cost approximately $20,000. Currently there are about 200,000 dialysis machines being used around the world, with only a small percentage of these machines being capable of performing hemodiafiltration with online substitution fluid. Because hemodiafiltration provides a better treatment over current hemodialysis, there exists a clear need for a clinical practitioner to offer this mode of renal replacement therapy to his/her patients. As an alternative to purchasing a new hemodiafiltration machine (e.g., capable of producing online substitution fluid), the present applicants have developed a hemodiafiltration delivery module that enables online hemodiafiltration to be performed safely with an existing ultrafiltration (UF) controlled dialysis machine (U.S. Pat. No. 6,916,424 which is incorporated by reference in its entirety). The embodiments of a hemodiafiltration delivery module described generally included a flow meter or flow switch as a means to detect when the dialysate flow and/or blood flow had been stopped by the host dialysis machine, this enabling a control unit in the hemodiafiltration delivery module to stop the substitution fluid pump. Additional means are described using various detection devices to determine when the blood pump has stopped, which include optical, vibrational, and inductive based sensors. Though pressure sensors are described in this patent, these pressure sensors are not used as the primary input to control the operation of the substitution pump. It is recognized in this application, however, that a simplification of the control scheme resulting from the elimination of the number of sensors and/or the use of a single type sensor is preferred from a reliability and cost perspective.

SUMMARY

This invention provides a method and apparatus for a hemodiafiltration delivery module that is used in conjunction with a UF controlled dialysis machine to enable hemodiafiltration therapy to be performed. The advantage is that one can fully utilize a current functioning dialysis machine to perform a hemodiafiltration therapy as opposed to purchasing a completely new machine that offers this capability.

It is an object of the present invention to overcome safety issues that arise when there is no coordination between dialysis machine events (e.g., alarm conditions, mode shifts, etc.) and an externally controlled substitution fluid pump. In particular, it is an object of the invention to prevent potentially unsafe or hazardous conditions, such as can occur when the substitution pump continues to pump fluid after the blood pump on the dialysis machine stops circulating blood through the extracorporeal circuit or after the dialysis machine stops delivering dialysate fluid to the substitution pump and dialyzer.

According to an aspect of the invention, the hemodiafiltration delivery module is used in conjunction with a dialysis machine that provides ultrafiltration (UF) control as is known in the art, for example the Fresenius 2008 series dialysis machine available from Fresenius Medical Care, Lexington, Mass. In addition, a sterilizing filter cartridge containing at least one filtration stage is used to filter the non-sterile dialysate solution and thus render it sterile and non-pyrogenic. The sterilizing filter cartridge may contain a redundant filter stage as an added measure of safety, i.e. should one of the filters fail during the hemodiafiltration treatment. The configuration is such that fresh dialysate from the dialysis machine passes through the hemodiafiltration delivery module prior to being delivered to the dialyzer cartridge. A portion of this dialysate fluid is drawn off from the dialysate stream by the hemodiafiltration delivery module and is passed through the sterilizing filter (or filters) by use of a substitution pump. The sterilizing filter cartridge effectively removes bacteria that may be present in the dialysate fluid. In addition, endotoxins and other particulate material are also effectively filtered out of the dialysate to make the dialysate fluid non-pyrogenic and of suitable injectable quality. The sterile filtered dialysate fluid is then introduced into the extracorporeal circuit as a substitution fluid for hemodiafiltration via an infusion tubing segment connecting the outlet port of the final sterilizing filter and an inlet port of the extracorporeal circuit. Due to the UF control system (which includes dialysate flow balancing components), a substantially equal volume of plasma water will be filtered across the dialyzer membrane into the dialysate compartment to make up for the "missing" volume of dialysate fluid that is drawn off by the hemodiafiltration delivery module. As indicated above, the dialysate fluid that is not used as substitution fluid is reintroduced into the dialysate compartment of the dialyzer. Generally speaking, the process of removing and filtering a portion of dialysate fluid for use as a sterile fluid that is infused into the extracorporeal circuit as a substitution fluid is known in the art as "online hemodiafiltration".

During normal operation of the presently disclosed system and when performing a hemodiafiltration treatment, the hemodiafiltration delivery module monitors at least two parameters to assure that the hemodiafiltration process can be safely carried out. One parameter is associated with an adequate flow of dialysate through the hemodiafiltration delivery module, such that sufficient substitution fluid can be generated. The other parameter is associated with an adequate flow of blood through the extracorporeal circuit. The latter is meant to assure that the blood does not become hemoconcentrated as it passes through the dialyzer portion of the circuit. If this occurs, it can result in blood clotting in the dialyzer and a subsequent reduction of performance. In a first embodiment of the invention, a one-way check valve in combination with two pressure sensors are used to detect when dialysate flow has stopped or when the blood flow rate has diminished to an undesirable level (i.e., below a pre-defined threshold). Outputs from these pressure sensors are used in a feedback control loop to control the substitution pump speed. In a second embodiment of the invention, a one-way check valve in combination with a pressure sensor is used to detect for an adequate dialysate flow, while blood flow is detected by oscillatory pressure waves sensed in an air pressure cuff that is fitted around a section of bloodline tubing distal to the peristaltic blood pump. An added feature of these embodiments is that it the fluid path, including the sterilizing filter(s), can be configured as a completely disposable set which minimizes maintenance time associated with cleaning and disinfecting the fluid path between uses. In addition, another benefit of the present invention is that the module has a simple construction that allows for easy attachment and integration into existing dialysis systems and also has more optimal line (conduit) management due to reduced length lines, etc., which advantageously reduces the tangling of lines, etc.

DETAILED DESCRIPTION OF PREFERRED EMBODIMENTS

Figure 1:
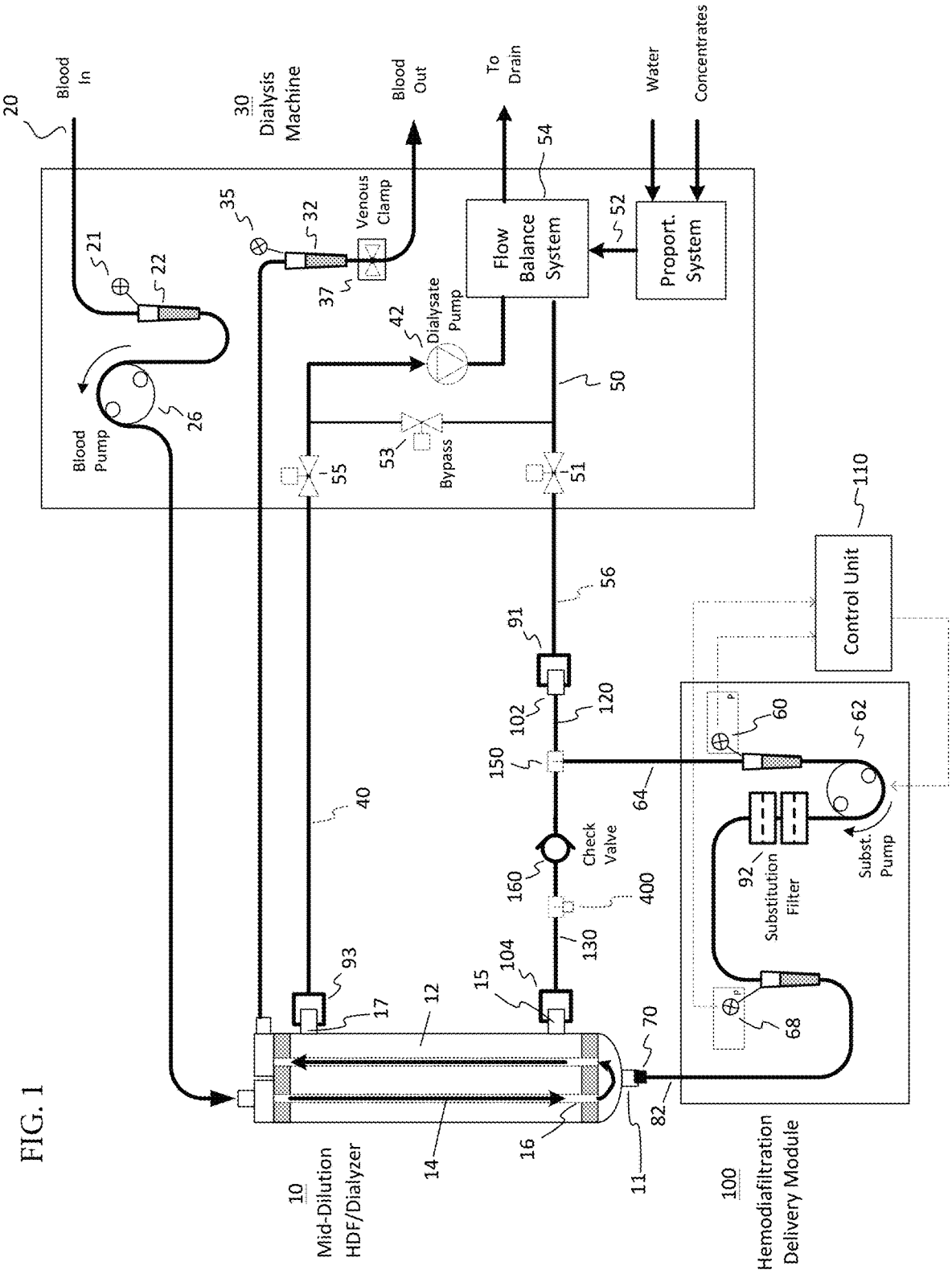
FIG. 1 is a schematic illustration of a hemodiafiltration delivery module and sterilizing filter configured with a dialysis machine for hemodiafiltration treatment in accordance with one embodiment.

In the embodiment of FIG. 1, blood to be cleaned 20 is pumped by a blood pump 26 and enters a dialyzer cartridge 10. As shown in FIG. 1, inlet blood circuit pressure may be measured upon entering the blood pump 26 by use of an arterial drip chamber 22 in the blood circuit. As known in the art, inlet arterial blood pressure may be measured via a pressure transducer line 21 that extends from the drip chamber 22 to a pressure monitoring port on the dialysis machine 30. Some bloodlines use a chamber containing a flexible diaphragm to monitor pressure in the bloodline, whereby the flexible diaphragm prevents the pressure monitoring port from being contaminated and vice versa. The blood carrying tubing, known in the art as an arterial bloodline, may be made of a flexible polyvinylchloride (PVC) tubing. The blood flow rate is generally in the range of about 200 to about 700 ml/min, preferably 300 to 600 ml/min.

Dialyzer cartridge 10 contains a semi-permeable membrane 16 that divides the dialyzer cartridge 10 into a blood compartment 14 and a dialysate compartment 12. As blood passes through the blood compartment 14, plasma water containing blood substances may be filtered across the semi-permeable membrane 16. Additional blood substances are transferred across the semi-permeable membrane 16 by diffusion which is induced by a difference in concentration between the blood compartment 14 and the dialysate compartment 12. The dialyzer cartridge 10 used may be of any type suitable for hemodialysis, hemodiafiltration, hemofiltration, or hemoconcentration, as are known in the art. Preferably, the dialyzer cartridge 10 contains a high flux membrane and includes a substitution fluid port 11 for mid-dilution HDF. Examples of suitable cartridges 10 include but are not limited to the Nephros MD220, Fresenius F80, Baxter CT 110, Hospal Filtral 16, or Minntech Hemocor HPH 1000.

Figure 4:
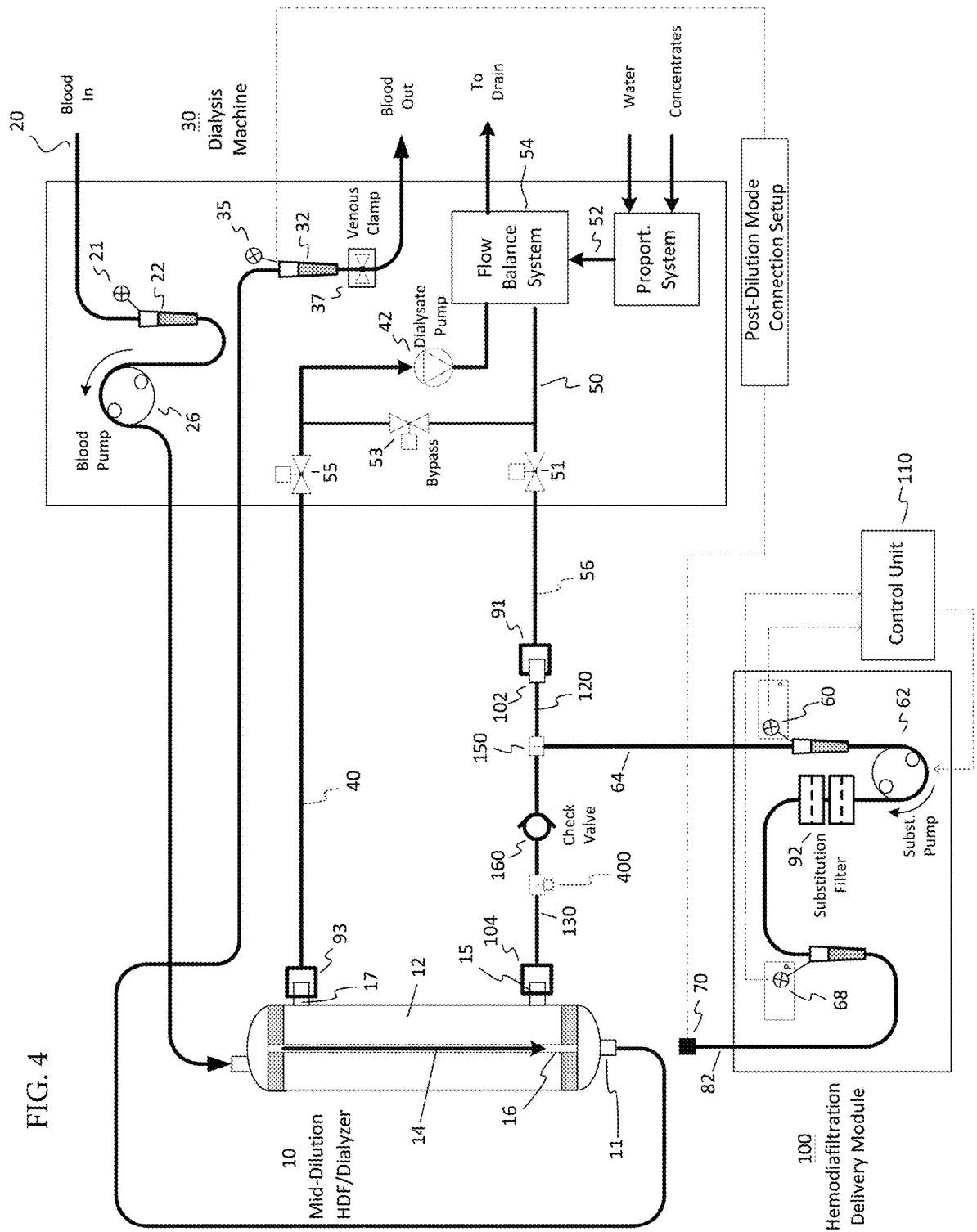
FIG. 4 is a schematic illustration of a hemodiafiltration delivery module and sterilizing filter configured with a dialysis machine for hemodiafiltration treatment in accordance with one embodiment and depicting a post-dilution substitution delivery scheme.
Figure 5:
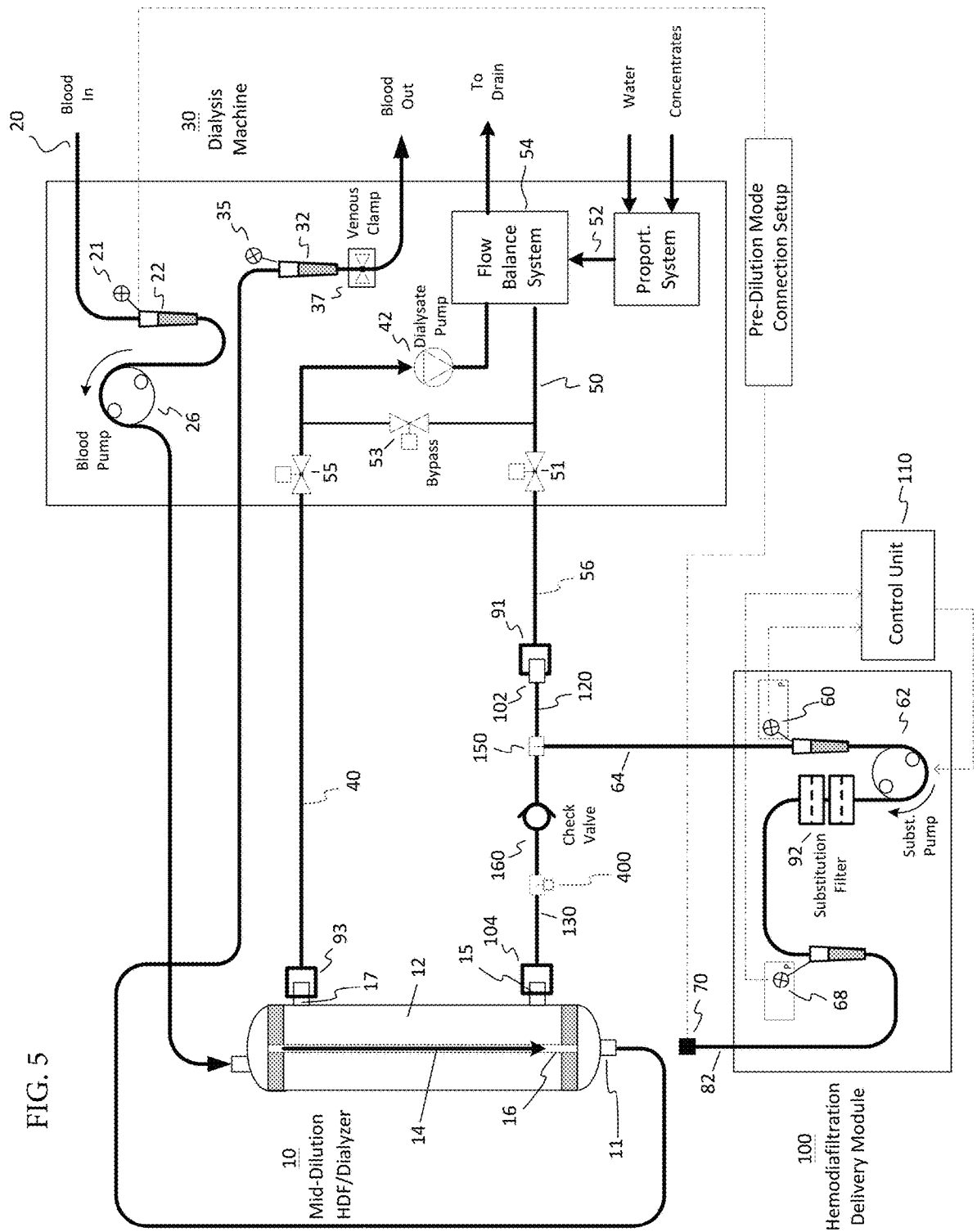
FIG. 5 is a schematic illustration of a hemodiafiltration delivery module and sterilizing filter configured with a dialysis machine for hemodiafiltration treatment in accordance with one embodiment and depicting a pre-dilution substitution delivery scheme.

Blood that has been purified then exits the dialyzer cartridge 10 and flows through a second blood carrying tubing, known in the art as a venous bloodline. The venous bloodline may use a drip chamber 32 as a means to measure blood circuit pressure downstream of the dialyzer cartridge 10. In a similar fashion to the arterial bloodline, venous blood pressure is measured via a pressure transducer line 35 that extends from the drip chamber 32 to a pressure monitoring port on the dialysis machine 30. As shown in FIG. 1, substitution fluid that has been generated by a hemodiafiltration delivery module 100 is introduced into the substitution fluid port 11 of the dialyzer 10. This configuration is known in the art as a mid-dilution hemodiafiltration mode. It should be understood by those skilled in the art that the substitution fluid may be introduced into any suitable connection of the blood circuit. For example, and as described in more detail below, it may be introduced into the arterial drip chamber 22 in a pre-dilution hemodiafiltration mode (FIG. 5), or it may be introduced in the venous drip chamber 32 in a post-dilution hemodiafiltration mode (FIG. 4). Fresh dialysate solution prepared by the dialysis machine may be accomplished using any method known in the art, for example the volumetric proportioning method used in the Fresenius 2008 dialysis machine, available from Fresenius, Lexington, Mass., USA. Dialysate fluid is conveyed to a flow balancing system 54 via fluid path 52. The flow balancing system 54 may include any suitable devices known in the art, for example, volumetric balance chambers as used in the Fresenius 2008 dialysis machine, or dual flow meters as used in the Baxter 1550 dialysis machine, available from Baxter, Deerfield, Ill., USA. Fresh dialysate from the flow balance system 54 flows through a conduit 50 that leads to the hemodiafiltration delivery module 100. Connection to the hemodiafiltration delivery module 100 is accomplished by connecting the dialysis machine Hansen connector 91 to a suitable mating port 102 on the hemodiafiltration delivery module 100. The fresh dialysate solution generally flows through a conduit 120 of the hemodiafiltration delivery module 100 and exits the module via conduit 130 that connects to the inlet dialysate port 15 of the dialyzer cartridge 10 via connector 104. Conduit 130 includes a one-way check valve 160 such that direction of fresh dialysate only goes toward the inlet dialysate port 15.

Spent dialysate exits the dialyzer cartridge 10 though a dialysate outlet port 17 and flows through a conduit 40 that is connected to the dialysate port 17 via a Hansen connector 93 as known in the art. The spent dialysate, which may be considered a mixture of dialysate, plasma water, and blood toxins that have crossed the semi-permeable membrane 16 of the dialyzer cartridge 10, is returned to the flow balancing system 54 via a dialysate pump 42. For ultrafiltration control purposes, a UF pump (not shows) may be used to bypass the flow balancing system as a means to remove a specified volume of fluid from the patient during the treatment. The dialysis machine generally includes a series of valves, such as indicated by valves 51, 53, and 55, which are used to shunt or divert dialysate away from the dialyzer. This is commonly known in the art as a "bypass mode" or a "cartridge isolate mode".

To generate sterile substitution fluid "online", a portion of the fresh dialysate fluid flowing through conduit 120 of the hemodiafiltration delivery module 100 is drawn off by a substitution pump 62 via conduit 64. This portion of dialysate is pumped into conduit that leads to the sterilizing filter(s) 92 (indicated as "Substitution Filter" in FIG. 1). As shown, the substitution filter may include redundant sterilizing filters that are connected in a series arrangement as an extra safety precaution (i.e. should one of the filters fail during the treatment). The function of the substitution fluid filter 92 is to remove bacteria, endotoxins, and particulate from the dialysate fluid to render it suitable for injection into the blood circuit. After the dialysate fluid is passed through the substitution fluid filter 92, it flows through a flexible tubing conduit 82 that is connected to the blood circuit via connector 70.

Basic operation of the hemodiafiltration delivery module during a treatment is further described with reference to FIG. 1 which illustrates a control aspect of an embodiment of the invention. First, two inputs are used as feedback control inputs to control unit 110 that enables operation of the substitution pump 62. As described herein, operation of the substitution pump 62 can be stopped upon detection of certain events and conversely, the substitution pump 62 can be restarted upon detection of certain events. These inputs include a pre-substitution pump pressure transducer (a first pressure sensor) 60 that monitors inlet pressure of the substitution pump 62 (and is thus located upstream of the pump 62) and a post-substitution filter pressure transducer (a second pressure sensor) 68 that monitors substitution fluid pressure prior to entering the extracorporeal blood circuit (and is thus located downstream of both the filter 92 and pump 62).

To those skilled in the art, this arrangement of the first and second pressure sensors 60, 68 enables one to monitor the dialysate fluid and blood flow of the host hemodialysis system (machine 30). When the dialysate fluid flow goes into the bypass mode, the check valve 160 on the dialysate line 120, 130 causes the module pre-pump pressure to go to a large negative value since there is no flow to feed the substitution pump 62. This detected by the first pressure sensor 60 that is located upstream of the pump 62 and is detected as a drop in pressure along conduit 64 and more particularly, is detected as a drop in pressure below a prescribe threshold pressure value (indicative of a lack of requisite fluid flow in conduit 64). The HDF module 100 can react by stopping the HDF (substitution) pump 62 in order to prevent unnecessary wear on the peristaltic section.

When the blood flow of the host hemodialysis machine 30 stops, the pressure at the mid-dilution point (a location at connector 11) of the dialyzer 10 decreases due to decreased blood flow through the fibers and this drop in pressure can be sensed by the post filter pressure sensor 68 (the second pressure sensor). In other words, when the blood flow is stopped or substantially reduced, the second pressure sensor 68 detects a drop in pressure in the segment of the conduit 64 in which the second pressure sensor 68 is located. The HDF module 100 can then stop the HDF pump 62 in response to this condition. A person of skill in the art can also see that the post filter pressure sensor 68 can sense blood flow rates intermediate between stopped and full treatment flow rates thus allowing the HDF module 100 to slow the HDF pump 62 in response to the decreased blood flow. In other words, if the blood flow rate is substantially decreased but blood is still flowing, the module 100 can instruct the pump 62 to operate at a slower speed in view of the level of decreased blood flow.

Furthermore, a person of skill in the art can also see that restarting the host hemodialysis dialysate flow can be sensed by a more positive pressure excursion of the pre-pump pressure (detected by the first pressure sensor 60) signifying to the HDF module 100 that the HDF pump 62 may resume operation. In other words, the control unit 110 can continuously monitors the state of the pump 62 and the pressure readings at the first pressure sensor 60 and the second pressure sensor 68 and thus, after the pump 62 has been stopped due to a detection of one of the events described previously, the control unit 110 then monitors the pressure at the first pressure sensor 60 for evidence that the flow of dialysate fluid has resumed (indicating an end to the bypass mode) and in response the control unit 110 can instruct the pump 62 to operate resulting in the resumed generation of substitution fluid.

A person of skill in the art can also see that this will create a pressure in the post-filter line (segment of conduit 64 located downstream of the filter 92) that can be used to determine whether the host hemodialysis blood pump 26 is operating. Testing has shown that the pre-pump pressure (detected at the first sensor 60) also exhibits characteristics that sense whether the host hemodialysis system blood pump 62 is operating and thus the HDF module 100 can use that signal to determine whether to commence substitution fluid flow.

Still referring to FIG. 1, assume that hemodiafiltration is being performed whereby the dialysis machine 30 is producing 600 ml/min of fresh dialysate and the blood pump 26 is running at 400 ml/min. Further, the hemodiafiltration delivery module is drawing off 200 ml/min of fresh dialysate from conduit 120 via a tee connector 150 and pushing it through the substitution filter and into the substitution port 11 of the mid-dilution dialyzer 10. The remaining 400 ml/min of fresh dialysate then passes through conduit 130, which includes the check-valve 160, and into the inlet dialysate port 15. As 600 ml/min of spent dialysate is needed to satisfy the flow balancing system of the dialysis machine, the dialysate pump 42 operates so that 200 ml/min of plasma water is conducted across the dialyzer membrane. Assume then that the dialysis machine goes into a bypass state (mode) which stops the flow of dialysate to and from the dialyzer 10 by closure of valves 51 and 55, while simultaneously opening bypass valve 53. As soon as this occurs, the pressure at the first pressure sensor 60 goes in a negative direction as dialysate fluid no longer is available from the dialysis machine 30 via conduit 120. In addition, the position of the one-way check valve 160 in conduit 130 prevents retrograde flow of dialysate from the dialysate compartment 16 of the dialyzer. The result is that the detected pressure at the first pressure sensor 60 falls below a threshold pressure value and operation of the substitution pump 62 is stopped. Upon re-establishment of the dialysate fluid flow from the dialysis machine 30, valves 51 and 55 are opened with valve 53 being closed, the pre-substitution pump pressure detected at the first pressure sensor 60 will increase. Upon detection that the detected pressure at the location of the first pressure sensor 60 is above the threshold value, the substitution pump 62 is enabled to return back to hemodiafiltration. An algorithm may be used to control a time delay and/or ramp up rate of the substitution pump to minimize rapid changes of blood and dialysate pressures being monitored by the dialysis machine. Such functionality can be considered to be part of an auto restart feature.

For the situation in which the blood pump 26 is stopped during the HDF treatment, such as due to an arterial blood pressure alarm or if air is detected in the venous drip chamber 32 causing an alarm on the dialysis machine, it is known to those skilled in the art that a venous clamp 37 located below the venous drip chamber 32 is also closed to put the dialysis machine in a safe state. When this occurs, blood can no longer enter or leave the dialyzer 10. As previously mentioned, when the blood pump 26 stops operating, a pressure drop is detected by the second pressure sensor 68 that is located downstream of the filter 92. If the substitution fluid continues to run, such as at the 200 ml/min flow rate described above, a portion of the blood inside the dialyzer 10 may continue to be hemodiafiltered provided plasma water from the blood can pass through the dialyzer membrane 16 at a rate equal to the 200 ml/min substitution fluid rate. It can be anticipated that some hemoconcentration of red blood cells can occur in the dialyzer depending upon where the substitution fluid is being introduced into the extracorporeal circuit and the differences of pressure along the length of the dialyzer. The present invention addresses this concern by having control unit 110 continuously monitor the detected pressures at the location of the second pressure sensor 68 and in the event that the detected pressure falls below a threshold value (which is indicative that the blood pump 26 has stopped operating), the control unit 110 stops operation of the substitution pump 92 and substitution fluid is no longer delivered to dialyzer 10. Upon re-establishment of the blood flow (as detected at least by a pressure increase at the location of the second pressure sensor 68 and above the threshold value or by a pressure in crease at the location of the first pressure sensor 60 as described previously), the substitution pump 62 can be restarted. The control unit 110 can also be configured to use an algorithm to control a time delay and/or ramp up rate of the substitution pump 62 to minimize rapid changes of blood and dialysate pressures being monitored by the dialysis machine 30.

An added feature of this embodiment, and the ones to follow, is that it the fluid path, including the sterilizing filter(s), can be configured as a completely disposable set which minimizes maintenance time associated with cleaning and disinfecting the fluid path between uses.

Figure 2:
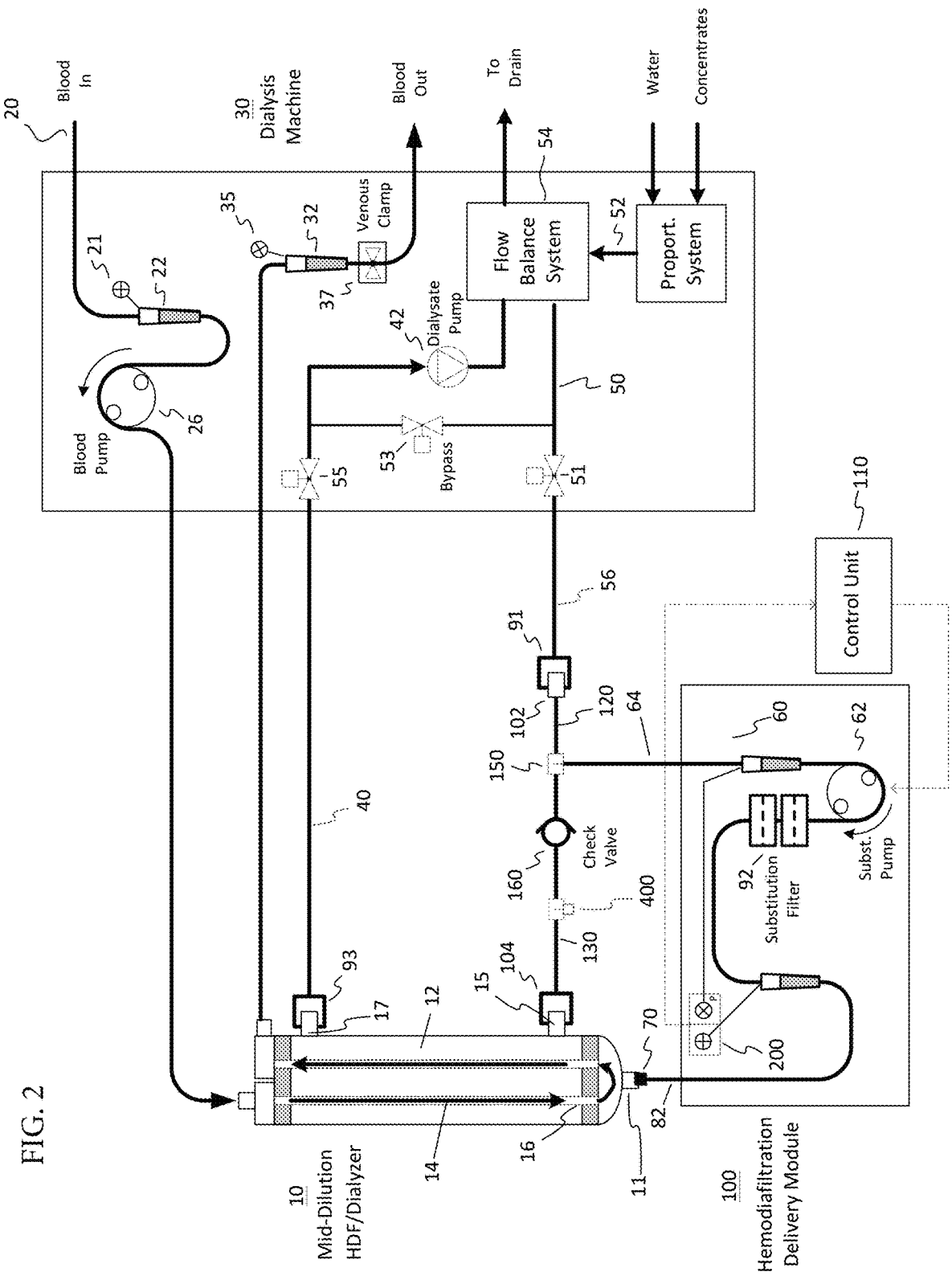
FIG. 2 is a schematic illustration of a hemodiafiltration delivery module and sterilizing filter configured with a dialysis machine for hemodiafiltration treatment in accordance with an embodiment of the invention depicting a differential pressure sensor for blood and dialysate flow detection.
Figure 3:
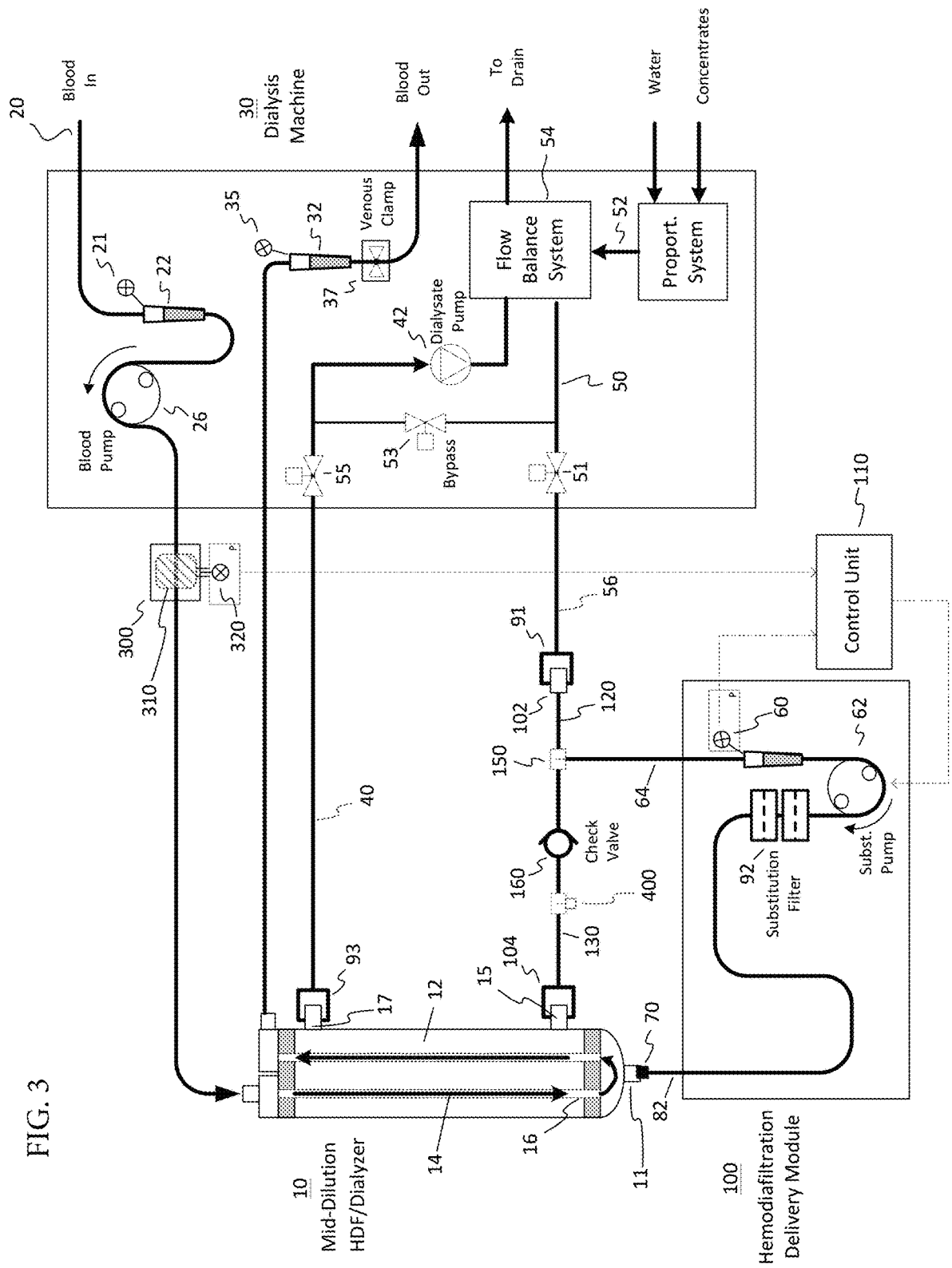
FIG. 3 is a schematic illustration of a hemodiafiltration delivery module and sterilizing filter configured with a dialysis machine for hemodiafiltration treatment in accordance with an embodiment of the invention depicting an oscillatory pressure detection device for detecting blood flow.

A second embodiment of the invention is described with reference to FIG. 2. Here, a differential pressure transducer 200, as is known in the art, is used to replace to replace the two separate pressure sensors, this having the advantage of eliminating one of the components which reduces the cost and may improve the reliability of the unit. In any event, the transducer can operate similar to the first embodiment in which a pre substitution pump pressure and a post substitution filter pressure are monitored as a means for controlling the operation of the substitution pump 62 A third embodiment of the invention is described with reference to FIG. 3. The difference between this embodiment and the first embodiment is the manner in which dialysate flow and blood flow is sensed by the hemodiafiltration delivery module 100. Here, dialysate flow is sensed by a single pre-substitution pump pressure sensor 60 in combination with the use of a one-way check valve 160 in conduit 130. In this case, when the dialysis machine goes into a bypass state which stops the flow of dialysate to and from the dialyzer by closure of valves 51 and 55, while simultaneously opening bypass valve 53, the pressure at pressure sensor 60 goes in a negative direction as dialysate fluid no longer is available from the dialysis machine via conduit 120. As indicated before, the position of the one-way check valve 160 in conduit 130 prevents retrograde flow of dialysate from the dialysate compartment 16 of the dialyzer. The result is a condition whereby the pre-substitution pump pressure sensor 60, as measured by the hemodiafiltration delivery module, is decreased to below a threshold value that turns OFF the substitution pump 62, thereby putting the system in a safe state. Upon re-establishment of the dialysate flow from the dialysis machine, valves 51 and 55 are opened with 53 being closed, the pre-substitution pump pressure sensor 60 will increase. Once it returns back into the acceptable operating range, the substitution pump 62 is enabled to return back to hemodiafiltration. An algorithm may be used to control a time delay and/or ramp up rate of the substitution pump to minimize rapid changes of blood and dialysate pressures being monitored by the dialysis machine.

For blood flow sensing, according to the third embodiment, an oscillatory pressure detection device 300 is used to sense pressure pulses in the bloodline as the result of the peristaltic nature of the roller type blood pump 26. The oscillatory pressure detection method is commonly used for automated measurements of systolic and diastolic blood pressure in humans as an alternative to the auscultatory method as known in the art. This method utilizes a pressure cuff 310 surrounding a section of the bloodline whereby the cuff can be inflated to a point such that pressure oscillations (caused by the intermittent pressure pulses when the blood pump is running) are detected by a pressure sensor 320 in fluid communication with the pressure cuff. The advantage of this method over use of a strain gauge in direct contact with the bloodline as described in U.S. Pat. No. 6,916,424 is that it is less susceptible to external noise. For control purposes, the time interval between successive pressure oscillations can be used as a feedback control input to the control unit 110. If no oscillations are detected, or if the time period waiting for a next pressure oscillation exceeds a pre-set value, the substitution pump 62 can be turned OFF and the system put in a safe state. Once pressure oscillations are detected when the blood is restarted, the substitution pump 62 is enabled to return back to hemodiafiltration. An algorithm may be used to control a time delay and/or ramp up rate of the substitution pump to minimize rapid changes of blood and dialysate pressures being monitored by the dialysis machine.

System Priming Operation

Referring again to FIGS. 1-3, another aspect of the present invention is that the hemodiafiltration delivery module 100 can be used as part of a priming operation for removal of air from the system. For example, as shown in the figures, an infusion port 400 can be provided along the conduit 130 between the connector 104 and the check valve 160. The infusion port 400 can take any number of different forms including but not limited to a tee connector that has two legs connected to segments of conduit 130 a third leg configured for selective attachment to the flexible tubing conduit 82 when a priming operation is desired. As described herein, the connection of the flexible tubing conduit 82 to the infusion port 400 is performed during a priming operation for removal of air in the conduit 64. The infusion port 400 can include a luer type construction to allow for each attachment to one end of the flexible tubing conduit 82.

In particular, to prime the system, one end of the flexible tubing conduit 82 is connected to the connector 150 at conduit 120 and other end of the flexible tubing conduit 82 is connected to the infusion port 400. During the initial attachment process, the flexible tubing conduit 82 is typically at least substantially full of air and is thus connected in-line with host HD dialysate flow. The HDF pump 62 is operated to pull fresh (air free) dialysate through the pump 62 and pushes through the substitution filter 92. The displaced air is injected with pressure back into the dialysate line 130 at infusion port 400 which is located downstream of the take-off (conduit 64) for the peristaltic pump 62 and is downstream of the check valve 160. Return to the dialysate flow substantially preserves fluid balance in the dialysate line without involving the blood side of the dialyzer. Minimization of air introduction to the blood side of the dialyzer reduces the time required to prepare the blood lines prior to connection to the patient.

The air infusion port 400 contains a check valve flowing in the direction of air infusion. This prevents any back flow of dialysate into a line that eventually connects to the patient blood circuit. Additionally, the check valve 160 in the dialysate flow line allows for immediate sensing of host HD machine dialysate flow cessation by way of a drop in pressure on the line (conduit 64) feeding the HDF peristaltic (substitution) pump 62. The first pressure sensor 60, which can be in the form of an integrated pressure pod, on the tube set 64 detects this pressure drop.

Similarly and as described herein the second pressure sensor 68 can be in the form of an integrated pressure pod 68 located after the substitution filter 92 (and after the substitution pump 62) to detect mid-dialyzer blood pressure which has a direct correlation to the blood flow rate (or stoppage of blood flow) of the Host HD machine 30. The ability to sense the dialysate and blood flow of the host HD machine using pressure pods 60, 68 on the HDF tube set (conduit 64) enable a parameter interface-free way for the HDF module 100 to sense the operational state of the host HD machine and to respond automatically.

By connecting the free end of the flexible tubing conduit 82 to the conduit 130, any air initially in the conduits (line segments) 64, 82 of the module 100 is delivered into the dialyzer 10 which is more suited for removing said air (bubbles). After running the machine during the priming operation and once air is removed from the conduits 64, 82, the flexible tubing conduit 82 is removed from the air infusion port 400 and is then connected to the substitution fluid port 11 of the dialyzer 10 and normal operation can begin.

Pre and Post-Dilution HD Mode

As previously mentioned, the module 100 can be used in both a pre and post-dilution HD scheme. For example, in a pre-dilution HD scheme shown in FIG. 5, the flexible tubing conduit 82 can be connected to the arterial drip chamber 22 instead of to the connector 11 of dialyzer 10 and similarly, in a post-dilution HD scheme shown in FIG. 4, the flexible tubing conduit 82 can be connected to the venous drip chamber 32 instead of to the connector 11 of the dialyzer 10.

It will be appreciated by persons skilled in the art to which this invention pertains that the invention is not limited to the preferred embodiments and configurations described above and with reference to the accompanying drawings.

What is claimed is:

1. In a blood dialysis system including a dialysis machine that includes a source of dialysate fluid and an extracorporeal circuit, a method of preventing flow of substitution fluid to the extracorporeal circuit comprising the steps of:

providing a hemodiafiltration module including a first conduit having a first end and a second end for carrying dialysate fluid and a second conduit in selective communication with the first conduit such that the second conduit selectively receives a diverted amount of the dialysate fluid, the hemodiafiltration module further including at least one sterilizing filter in fluid communication with the second conduit for filtering the diverted dialysate fluid to produce the substitution fluid, wherein a one-way check valve is disposed in the first conduit at a location downstream of where the dialysate fluid is diverted to the second conduit;

fluidly connecting the first end of the first conduit to the dialysis machine so that the dialysate fluid flows from the source of the dialysate fluid to the first conduit;

fluidly connecting the second conduit to the extracorporeal circuit such that the substitution fluid is delivered and introduced into the extracorporeal circuit;

providing a control unit;

detecting a first characteristic of the dialysate fluid flowing within one of the first conduit and the second conduit and detecting a second characteristic of the substitution fluid before the substitution fluid enters the extracorporeal circuit and at a location downstream of the at least one sterilizing filter; and inputting the detected first and second characteristics to the control unit, wherein the control unit is configured to prevent the flow and introduction of the substitution fluid into the extracorporeal circuit when at least one of: (1) the first characteristic meets a first prescribed criteria, wherein the first characteristic comprises a pressure of the dialysate fluid and (2) the second characteristic meets a second prescribed criteria, the second characteristic comprising a pressure of the substitution fluid at the location downstream of the at least one sterilizing filter.

2. The method of claim 1, further including the step of: disposing a substitution fluid pump within the second conduit for diverting the amount of the dialysate fluid from the first conduit to the second conduit, wherein the control unit prevents the substitution fluid from being introduced into the extracorporeal circuit by controlling operation of the substitution fluid pump.

3. The method of claim 1, wherein the first prescribed criteria comprises when the pressure of the dialysate fluid falls below a first prescribed pressure value and the second prescribed criteria comprises when the pressure of the substitution fluid falls below a second prescribed pressure value.

4. The method of claim 2, wherein the hemodiafiltration module includes a priming mode of operation in which one free end of the second conduit is fluidly connected to first conduit at a location downstream of the one-way check valve, whereby operation of the substitution fluid pump causes is operated to pull the dialysate fluid through the substitution pump and the dialysate fluid is conducted across a substitution filter to produce the substitution fluid and resulting in displaced air to be injected with pressure back into the first conduit at the infusion port.

5. The method according to claim 1, wherein the control unit is responsive to a flow rate of the blood, and the method further includes the step of preventing flow of substitution fluid to the extracorporeal circuit by controlling flow of the diverted dialysate fluid within the second conduit in the control module when at least the second detected characteristic meets a prescribed criteria.

6. The method according to claim 5, further including: an oscillatory pressure sensing device that is in contact with a portion of a blood inlet conduit defining the extracorporeal circuit, and the method includes the step of detecting pressure pulses in the extracorporeal circuit using the oscillatory pressure sensing device when blood is flowing in the extracorporeal circuit.

7. The method according to claim 1, wherein at least one of the first conduit, second conduit, and the at least one sterilizing filter is disposable after the hemodiafiltration performed.

8. The method according to claim 2, wherein the substitution pump comprises a peristaltic (roller) type pump which integrates with a flexible tubing segment contained as part of the second conduit.

9. The method according to claim 1, wherein an entire fluid path of the hemodiafiltration is disposable after the hemodiafiltration treatment is performed.

* * * * *